US009345469B2

(12) United States Patent
Mattchen

(10) Patent No.: US 9,345,469 B2
(45) Date of Patent: May 24, 2016

(54) VECTOR COMPRESSION SYSTEM

(71) Applicant: Terry Mattchen, Scottsdale, AZ (US)

(72) Inventor: Terry Mattchen, Scottsdale, AZ (US)

(*) Notice: Subject to any disclaimer, the term of this patent is extended or adjusted under 35 U.S.C. 154(b) by 427 days.

(21) Appl. No.: 13/829,031

(22) Filed: Mar. 14, 2013

(65) Prior Publication Data

US 2014/0277194 A1 Sep. 18, 2014

(51) Int. Cl.
*A61B 17/064* (2006.01)
*A61B 17/04* (2006.01)
*A61B 17/68* (2006.01)
*A61B 17/06* (2006.01)
*A61B 17/84* (2006.01)

(52) U.S. Cl.
CPC ....... *A61B 17/0401* (2013.01); *A61B 17/06166* (2013.01); *A61B 17/68* (2013.01); *A61B 17/0642* (2013.01); *A61B 17/842* (2013.01); *A61B 2017/0409* (2013.01); *A61B 2017/0414* (2013.01); *A61B 2017/0459* (2013.01); *A61B 2017/0641* (2013.01)

(58) Field of Classification Search
CPC ............... A61B 2017/0419; A61B 2017/0641; A61B 17/0642; A61F 2/0811
USPC ..................... 606/75, 74, 232, 233
See application file for complete search history.

(56) References Cited

U.S. PATENT DOCUMENTS

| | | | | |
|---|---|---|---|---|
| 3,166,072 A * | 1/1965 | Sullivan, Jr. | .................. | 606/153 |
| 4,565,193 A * | 1/1986 | Streli | .................... | A61B 17/809 606/297 |
| 4,838,254 A * | 6/1989 | Gauthier | ......................... | 606/75 |
| 5,586,985 A * | 12/1996 | Putnam | ................ | A61B 17/809 606/281 |
| 5,961,521 A * | 10/1999 | Roger | ................... | A61F 2/0811 606/151 |
| 6,013,077 A * | 1/2000 | Harwin | .............. | A61B 17/0401 606/232 |
| 6,093,190 A * | 7/2000 | Mattchen | ........... | A61B 17/0401 606/74 |
| 6,755,831 B2 * | 6/2004 | Putnam | .............. | A61B 17/1728 606/102 |
| 7,267,682 B1 * | 9/2007 | Bender | ............. | A61B 17/0644 606/151 |
| 8,029,535 B2 * | 10/2011 | Ortiz | ................ | A61B 17/00234 227/175.1 |
| D691,720 S * | 10/2013 | Cheney | ........................ | D24/145 |
| 2004/0220574 A1 * | 11/2004 | Pelo et al. | ........................ | 606/73 |
| 2005/0010228 A1 * | 1/2005 | Medoff | ................ | A61B 17/809 606/74 |
| 2005/0192581 A1 * | 9/2005 | Molz et al. | ...................... | 606/74 |
| 2006/0058802 A1 * | 3/2006 | Kofoed | .............. | A61B 17/0642 606/75 |
| 2009/0054982 A1 * | 2/2009 | Cimino | ..................... | A61F 2/08 623/13.19 |
| 2011/0022099 A1 * | 1/2011 | Ashman | ........................ | 606/331 |
| 2011/0160766 A1 * | 6/2011 | Hendren | ............ | A61B 17/0487 606/232 |
| 2012/0130422 A1 * | 5/2012 | Hootstein | .......... | A61B 17/0401 606/228 |
| 2013/0184768 A1 * | 7/2013 | McIff | ................. | A61B 17/8685 606/301 |
| 2013/0315963 A1 * | 11/2013 | Erneta | ..................... | C08L 67/04 424/400 |
| 2015/0094762 A1 * | 4/2015 | Spenciner | ............ | A61F 2/0811 606/232 |

FOREIGN PATENT DOCUMENTS

FR 2638630 * 11/1988

* cited by examiner

*Primary Examiner* — David Bates
(74) *Attorney, Agent, or Firm* — Laura Tunnell

(57) ABSTRACT

The present invention is a new technology that addresses some of the deficiencies of current fracture fixation technology used in surgical procedures. It involves the use of a polymeric cored braided suture held in place by anchors implanted on each side of a fracture. The anchors must be secured into the bone while yet maintaining very high tensions in the suture during the deployment process. The polymeric cored braided suture is tensioned so as to compress the fracture and hold it in place, functioning as though it has sewn the bone fragment back together. This provides the rigid fixation of the fracture that is essential for primary healing to occur. Simultaneously, the tension preload provides compression which maintains fixation in the face of tensile and shear loads applied to the bone as a result of movement and weight bearing.

4 Claims, 6 Drawing Sheets

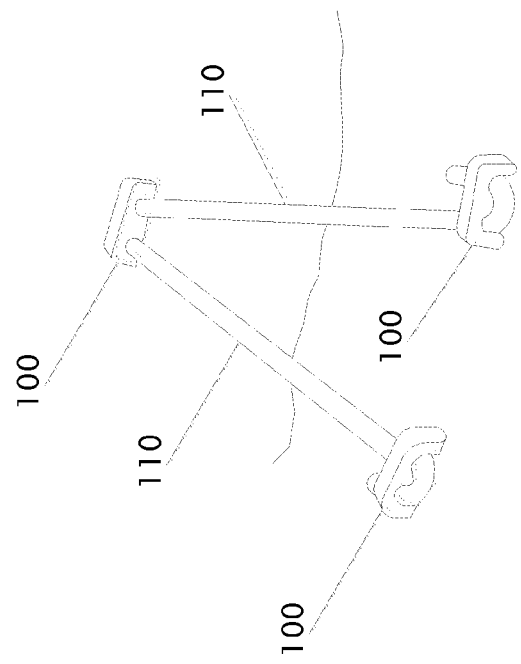
Fig. 1B
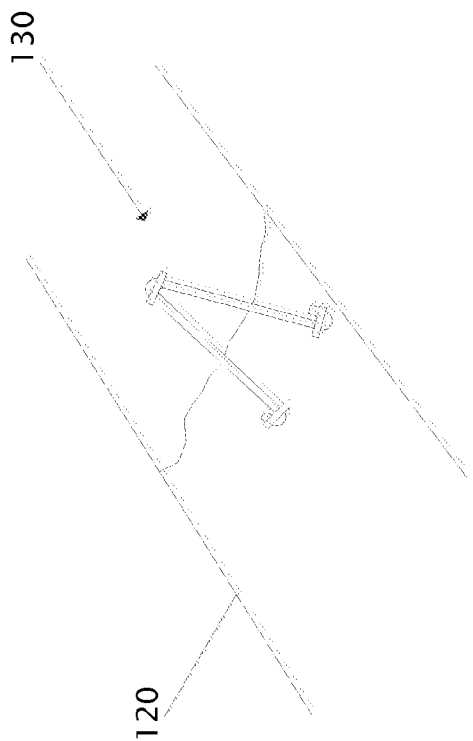
Fig. 1A
Figure 1

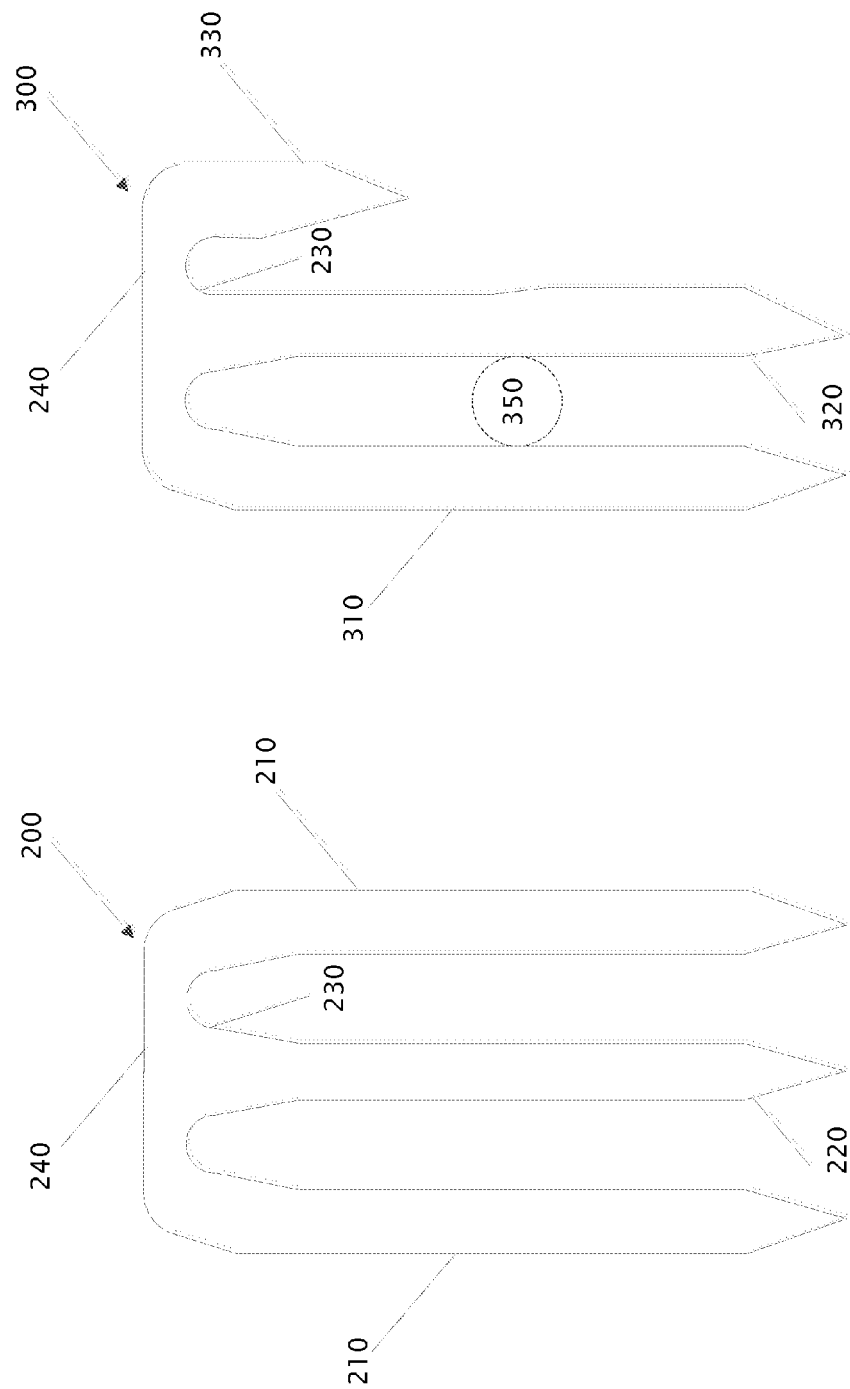

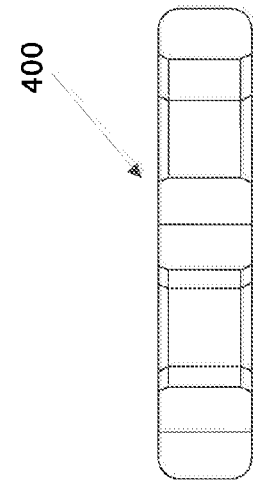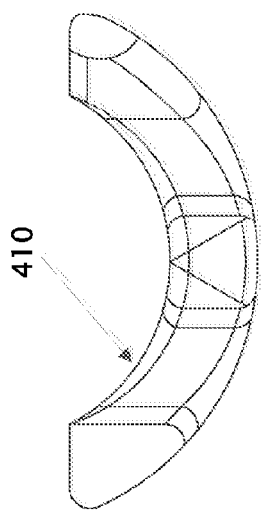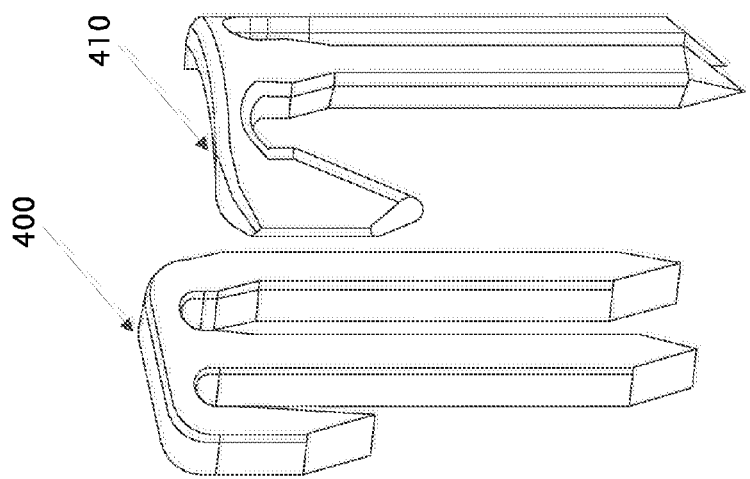
Figure 4

VECTOR COMPRESSION SYSTEM

The present invention involves devices and methods related to surgical bone fixation technology.

Bone is a remarkable material, and rare in its potential to heal completely following significant trauma. This potential is a product of the continuous remodeling that living bone undergoes and is only realized under conditions conducive to healing. The goal of the treatment of fractures is reduction of the fracture to as close to normal anatomy as possible and fixation that allows the bone to heal without complications. Better fixation promotes more rapid healing and allows earlier weight bearing. The present invention aims to satisfy these goals through new technology.

Bone can heal in two ways, primary and secondary healing. Primary healing is achieved by tunneling of osteoclasts; cells specialized to resorb bone, across the line of the fracture. This is followed by growth of blood vessels down the length of the tunnel and deposition of bone filling in the tunnel walls by osteoblasts, cells specialized in depositing bone. In this fashion, new bone is produced that spans the fracture and replaces the broken bone. Secondary healing proceeds by the formation of a callus, a large mass of collagen and granulation tissue. During this process, there is resorbtion of strained areas of bone adjacent to the fracture. Woven bone is deposited in the callus in an unstructured manner and is then remodeled by osteoclasts and osteoblasts to produce the healed bone.

Primary healing is desirable due to its lower risk of complications and potential for shorter healing time. However, it is possible only with absolute stabilization of the fracture by its fixation method. Proper fixation also reduces the risk of non-union, where the fracture fails to heal and fibrous tissue is instead produced. The reasons for this depends on the structure of bone and the way in which bone cells respond to the loads that are applied to the bone.

Current technology in internal fixation of fractures uses a variety of approaches. The most common of these are screws, compression plates, medullary nails, staples, and wires. These devices are made from a variety of materials whose properties are compared to bone in Table 1. Screws are usable in fractures where it is possible to drill a hole at an angle to the fracture so that the screw compresses the fracture as it is tightened. Compression plates are affixed in a way that spans the fracture and compresses the two pieces of bone together, placing the plate itself under tension. Medullary nails are rods driven into the medullary cavity of fractured long bones and serve to align the bone fragments while only partially bearing the load. Staples are driven into bone so that they span a fracture and provide fixation but do not apply any compression. Metal wires have been used to apply initial compression to fractures by tightening the metal wire in various lacing methods.

TABLE 1

Properties of Implant Materials and Bone

| Material | Elastic Modulus GPa | Yield Stress MPa | Ultimate Stress MPa | Fatigue Endurance MPa |
| --- | --- | --- | --- | --- |
| Ti—6Al—4V | 110 | 800 | 965 | 414 |
| 316L SS | 200 | 700 | 965 | 345 |
| Co—Cr—Mo (cast) | 210 | 450 | 655 | 310 |

All of these methods have shortcomings despite their clinical usefulness. Metal fixation devices all suffer from a mismatch in elasticity between the device and the bone that it is compressing. This results in a loss of compression with very minor amounts of bone resorbtion or device stretching. Nails, screws, wire, and plates are all prone to fatigue failure which leads to the need for further surgical intervention. Plates can also produce a stress-shielding effect, whereby the load is taken by the plate instead of the bone causing disuse-induced resorbtion and weakening of the bone. Screw holes act as stress risers in bone, leading to an increased risk of pathologic fractures. Aside from purely mechanical effects described above, plates and rods require relatively large incisions and disrupt either the periosteum or the medullary blood supply when it is needed most. Due to these shortcomings, there is an ongoing need for better fixation methods.

The present invention is a new technology that addresses some of the deficiencies of the current fracture fixation technology. It involves the use of a polymeric cored braided sutures (110) held in place by anchors (100) implanted in the bone (120) on each side of the fracture. The polymeric cored braided sutures (110) is tensioned so as to compress the fracture and hold it in place as shown in FIG. 1, functioning as though it has sewn the bone fragment back together. This gives rigid fixation of the fracture; essential for primary healing to take place. Simultaneously, the tension preload provides compression which maintains fixation in the face of tensile and shear loads applied to the bone as a result of movement and weight bearing.

Typically, there are four suture legs in a pattern and two patterns per fracture (one pattern on either side). If each suture leg is set to induce ten pounds of force across the anchors, for example, eighty pounds of cumulative force act to compress the bone fragments together during the healing process.

Any anchor in this type of system is challenged by the simultaneous need to:
1. maximize securement of the anchor into the bone, while
2. maintaining very high tensions in the suture as it is wound around the anchor.

Achieving a simultaneous optimum of these two goals presents an inherent conflict that is also addressed by the present invention.

The preferred suture of the present system is a prior art cable described in U.S. Pat. No. 6,589,246. It is comprised of a nylon monofilament core surrounded with a high-strength ultra-high molecular weight poly-ethylene braided jacket, giving it strength comparable to the highest strength multi-core steel cable while being much more flexible, fatigue resistant and abrasion resistant. The anchor of the present invention is capable of distributing the suture load into the bone while holding up to 100 pounds in shear. The deployment instrument of the present invention is designed to be used by the surgeon to place the anchors and set the compressive load in the suture. The latter is a rather complex device in that a single instrument supplies both the anchors and suture in a disposable cartridge. It must be packaged as an easily handled compact unit designed for the eventual goal of endoscopic use. It must have simple controls in order to be workable in a surgical environment. Additionally, the deployment instrument must:

Be able to drive the anchor in a controlled condition,
Be able to tension the suture to attain the desired compressive force,
Be able to set the compressive force so that the suture does not slip, and
Incorporate a disposable cartridge that attaches to a power unit wherein the suture and anchors are housed.

In summary, Several embodiments of a surgical anchor operable for securing surgical cable are disclosed. The basic surgical anchor comprises an essentially rotated "E" shaped staple having three prongs and a bridge. The three prongs are parallel to each other and define a longitudinal axis. The bridge is unitary with and perpendicular to each of the three prongs and defines a bridge axis that is perpendicular to the longitudinal axis.

The three prongs may further comprise a first outer prong, a middle prong, and a second outer prong. A first space is defined by the void between the first outer prong and the middle prong. The first space is also characterized by a first width, defined by the perpendicular distance between the first outer prong and the middle prong. A first arch defined by the first outer prong, the middle prong and the bridge. A second space is defined by the void between the second outer prong and the middle prong. The second space is also characterized by a second width, defined by the perpendicular distance between the second outer prong and the middle prong. A second arch defined by the second outer prong, the middle prong and the bridge. The first width is equal to the second width.

The first arch has a first shape that is an arc of a conical cross section. Likewise, the second arch has a second shape that is also an arc of a conical cross section. In one preferred embodiment, the first shape is identical to the second shape.

The first outer prong is may have a first length; the middle prong may have a middle length that is equal to the first length. The second outer prong may have a second length that is equal to both the first length and the middle length. Alternatively, the second outer length may be shorter than both the first length and the middle length by at least a distance equal to the second width.

In one embodiment, the rotated "E" shaped staple is flat. In another, the bridge axis of the rotated "E" shaped staple is shaped, the shape being defined by an arc of a conical cross section, most preferably of a circle, an ellipse, or a parabola. Either embodiment may have equal length prongs, or it may have two long prongs and one short prong as described above.

Any of the above described embodiments may include a surgical cable comprised of a polymer core and a braided jacket.

DESCRIPTION

List of Items in the Figures

100—anchor
110—polymeric cored braided suture
120—fractured bone
130—vector compression system
200—basic anchor
210—outer prong
220—middle prong
230—arch
240—bridge
300—vector compression anchor
310—long outer prong
320—long inner prong
330—short outer prong
350—cross section of a polymeric cored braided suture (110) shown in phantom
400—flat vector compression anchor
410—curved vector compression anchor
500—short prong (320) of the flat vector compression anchor (400) cutting into the polymeric cored braided suture (110)
510—short prong (320) of the curved vector compression anchor (410) clearing the polymeric cored braided suture (110)
600—exemplary deployment instrument
610—impulse motor
620—tensioning knob
630—tension release button
640—ratchet mechanism
650—suture drum
660—anchor magazine

DESCRIPTION OF THE FIGURES

Figure 5:
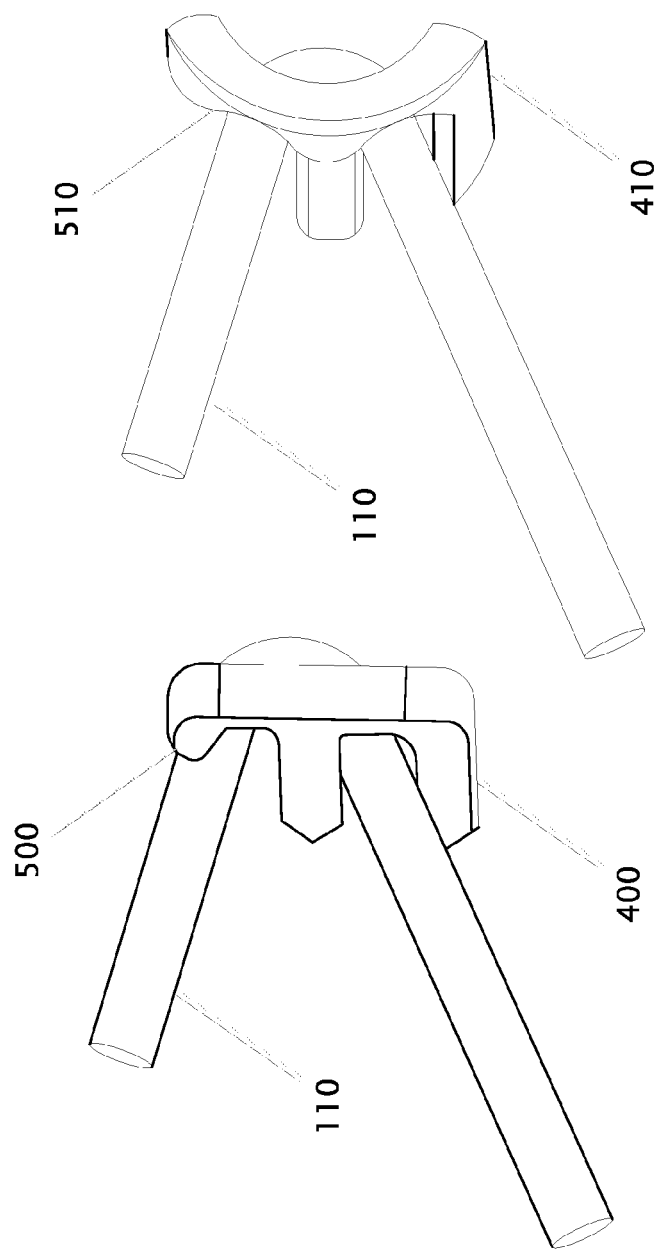

1.

FIG. 1: Illustrates the environment of the vector compression system (130). A fractured bone (120) is "sewn" together using a series of polymeric cored braided sutures (110) and anchors (100) placed on either side of the bone fracture as shown in FIG. 1A. FIG. 1B shows a close-up of the securement site. Although a simple "V" shaped pattern is shown in the figure, an I, N or W pattern is often used as well.

FIG. 2: An engineering drawing of the rotated "E" shaped geometry of a basic anchor (200) is shown. The basic anchor (200) has three prongs (210, 220) of equal length. An arch (230), defined by the space between the bridge (240) and each of the prong pairs, serves to further secure the polymeric cored braided sutures (110) when the basic anchor (200) is fully driven into the bone. The shape of the arch (230) is generally a conic section, most preferably an arc of a circle, ellipse, or parabola.

FIG. 3: An engineering drawing of the vector compression anchor (300) is shown, characterized by two long prongs (310, 320) and one short prong (330). A cross section (350) of a polymeric cored braided suture (110) is indicated in phantom in order to emphasize the importance of effecting a tight fit between the prongs (310, 320) and arch (230) of the vector compression anchor (300) and a polymeric cored braided suture (110).

FIG. 4: This figure shows two embodiments of the vector compression anchor (300). The first embodiment, FIGS. 4A and 4C, is flat (400), while the second embodiment, FIGS. 4B and 4D, is curved (410). The curve of the second embodiment is an arc of a conical section, most preferably a circle, ellipse, or parabola.

FIG. 5: Illustrates a comparative implementation of the two embodiments of FIG. 4. The notable differences in their relative performance can be seen by comparing the two regions indicated (500, 510), wherein the short prong (330) of the flat vector compression anchor (400) in FIG. 5A can be seen cutting into the polymeric cored braided suture (110), while the short prong (330) of the curved vector compression anchor (410) in FIG. 5B clears it.

Figure 6:
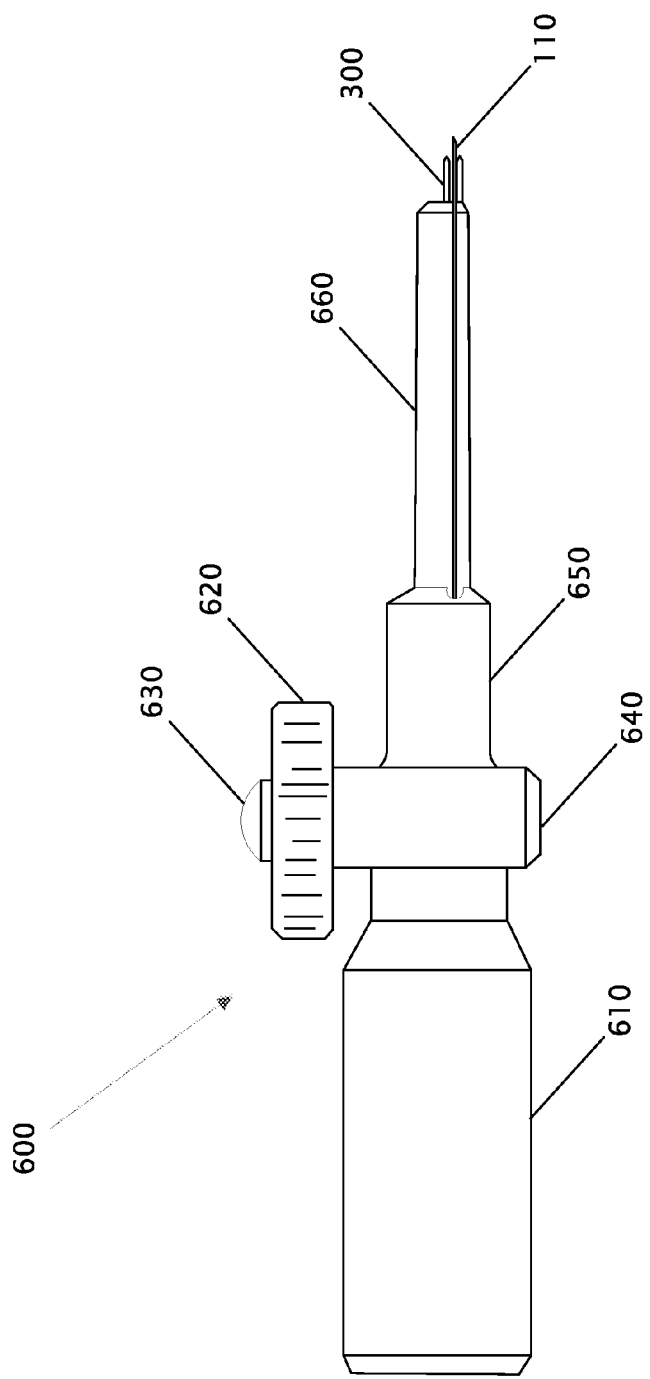

FIG. 6: Illustrates an exemplary deployment instrument (600) for housing and deploying sutures (110) and anchors (100) in a surgical environment.

Figure 7:
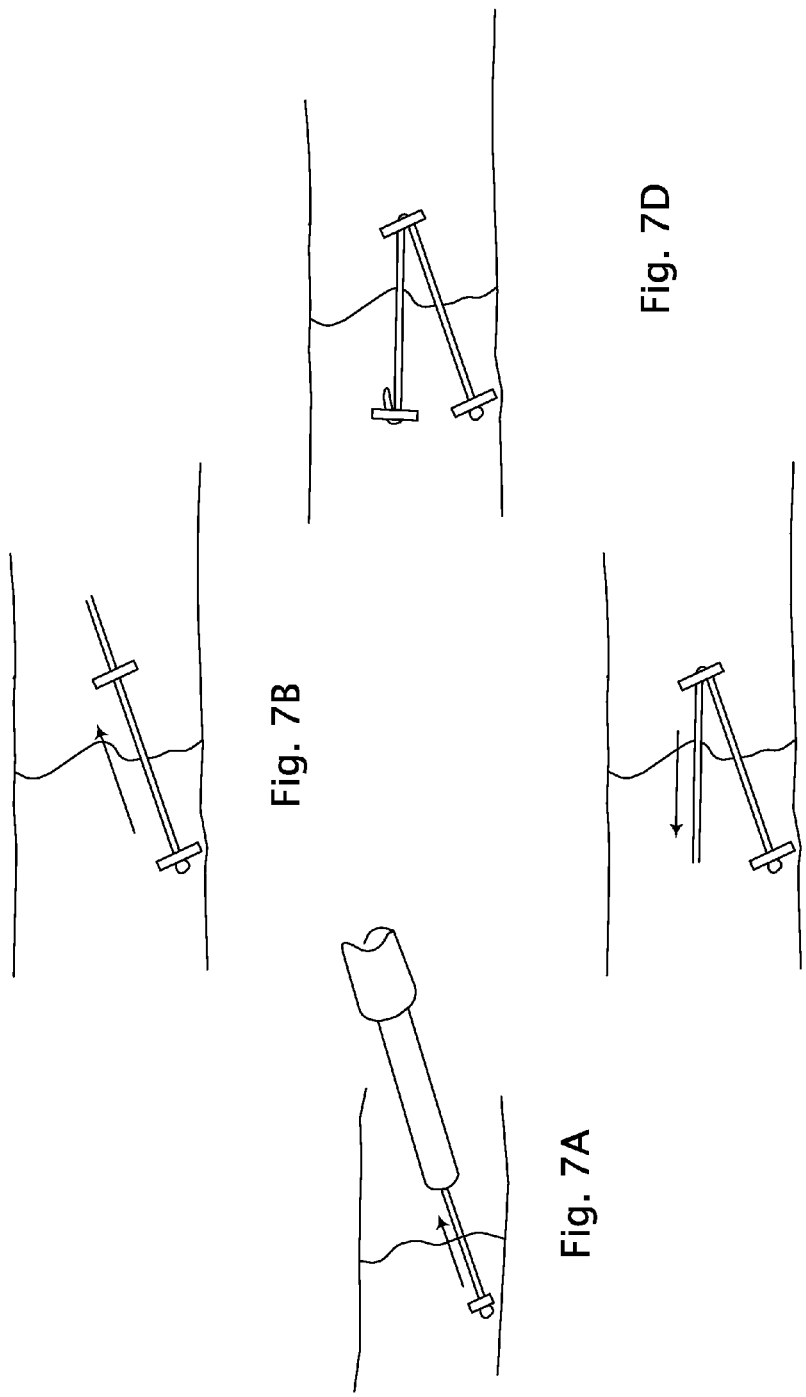

FIG. 7: The step-by-step process for constructing the exemplary pattern of FIG. 1 using the deployment instrument (600) of FIG. 6 is shown in FIGS. 7A-7D.

DETAILED DESCRIPTION OF THE PREFERRED EMBODIMENTS

The vector compression system (130) of FIG. 1 illustrates the basic environment of the present invention. A fractured bone (120) is "sewn" together using a series of polymeric cored braided sutures (110) and anchors (100) placed on either side of the bone fracture site. The present disclosure presents several embodiments of a novel design for the anchors (100) used in such a system.

FIG. 2 shows the rotated "E" shape of the basic anchor (200). In this embodiment, the anchor (100) is characterized by outside (210) and middle (220) prongs of equal length. By contrast, the vector compression anchor (300) of FIG. 3 has one long outside outer prong (310) that is equal in length to the long inner prong (320), and one short outside prong (330). The arch (230) defined by the space between the prongs and the bridge (240) can be rectangular, but a curve such as a circle, ellipse or parabola is preferred. In both embodiments of FIGS. 2-3, the spacing between the prongs as well as the arch (230) is tailored to tightly compress the polymeric cored braided suture (110) when the anchor (200, 300) is fully driven into the bone (120).

The vector compression anchor (300) of FIG. 3 is an evolutionary variation on the basic anchor (200) of FIG. 2. It addresses a fundamental problem encountered in the surgical environment; i.e., the need to decouple the simultaneous need for maintaining optimal tension in the suture (110) while providing optimal securement to the bone. As shown in FIG. 2, the prongs (210, 220) of a basic anchor (200) are equal in length. Consequently, a suture (110) cannot be wound around the middle prong (220) unless at least one outside prong (210) is not yet driven into the bone (120). However, in order to secure the basic anchor (200) into the bone (120), all three prongs (210, 220) must be driven into the bone at the same time. It is difficult decouple the two actions and thereby achieve optimization of the two goals.

The embodiment of FIG. 3 does indeed provide such a decoupling, thereby making it quite possible to achieve optimization of both goals. It enables all three prongs to be simultaneously driven into the while continuously maintaining optimal tension in the suture. Consider the steps necessary for deployment of a vector compression anchor (300) during a surgical procedure (as, for example, shown in FIG. 7):

1. The surgical cable (110) is threaded between the long outer prong (310) and the long inner prong (320).
2. The two prongs (310, 320) are then driven partly into the bone (120) at a depth that is adequate to secure the prongs (310, 320), yet shallow enough to allow wrapping of the cable (110) around the long inner prong (320) and through the space between the long inner prong (320) and the short outer prong (330).
3. The vector compression anchor (300) is then driven the remainder of the way into the bone, thereby securing the vector compression anchor (300) while never having the need to either compromise placement of the two long prongs (310, 320), nor allow a release of tension in the cable (110).

A direct line of force is maintained between one vector compression anchor (300) and the next in the "chain" as shown in FIGS. 1 and 7.

A further evolutionary variation of the vector compression anchor (300) is shown by considering FIGS. 4-5. FIG. 4 shows two embodiments of the vector compression anchor (300). FIGS. 4A and 4C illustrate a perspective and a top view, respectively, of a flat vector compression anchor (400), the advantages and deployment of which were discussed in the previous paragraph. FIGS. 4B and 4D illustrate a perspective and a top view, respectively, of a curved vector compression anchor (410).

The advantages of a curved vector compression anchor (410) over its flat counterpart can be seen by considering the comparisons shown in FIGS. 5A and 5B. Because the bridge (240) of the curved vector compression anchor (410) is curved, it straddles the suture (110) along a line more closely aligned with the suture's diameter. The flat compression anchor (400), on the other hand, straddles the suture (110) along a line more angled with respect to the suture's diameter. The straddling length of the latter is longer than the former. Recall from FIG. 3 that the prong (320, 330) spacing is roughly the diameter of the suture (110) for which it has been constructed in order to hold it as securely as possible without compromising structure. Thus, the shorter straddling length provided by the curved compression anchor (410) can be accommodated by the prong (320, 330) spacing. The longer length of the flat embodiment is simply too long and causes secondary problems such as cutting into the suture (110) structure. Consequently, the curved compression anchor (410) provides all the advantages of the flat compression anchor (400) as well as providing a better hold on the suture (110) without compromising its structure.

An exemplary deployment instrument (600) is shown in FIG. 6. As discussed in the introduction section of this application, an appropriate deployment instrument (600) must have the following attributes:

1) be packaged as an easily handled compact unit designed for the eventual goal of endoscopic use,
2) have simple controls in order to be workable in a surgical environment,
3) be able to drive the anchor in a controlled condition,
4) be able to tension the suture to attain the desired compressive force,
5) be able to set the compressive force so that the suture does not slip, and
6) incorporate a disposable cartridge that attaches to a power unit wherein the suture and anchors are housed.

The exemplary deployment instrument (600) must house the suture (110) and a set of about 5-6 vector compression anchors (300). It must be able to drive the anchor (300) into the bone effectively, thread the suture (110) between the anchors (300), apply the requisite level of tension in the suture (110), and effect a smooth transition to setting the next anchor (300) in an exemplary pattern such as is shown in FIGS. 1 and 7.

The instrument (600) is a generally cylindrical structure that incorporates an anchor magazine (660) for housing about 5-6 anchors (300). The suture drum (660) houses the suture (110). An impulse motor (610) serves to drive the anchors (300) into the bone. Tension is applied to the suture (110) via the tensioning knob (620) and ratchet mechanism (640). When the suture (110) has been adequately secured (300), the tension release button (630) is pressed in order to release tension on the suture (110) and proceed to the next step.

The step-by-step process for constructing the exemplary pattern of FIG. 1 using the deployment instrument (600) of FIG. 6 is shown in FIGS. 7A-7D. The deployment process is as follows:

2. As illustrated in FIG. 7A:
  a. The surgeon triggers the impulse motor (610) to set the first anchor (300).
  b. The suture (110) is fed from the anchor magazine (660) and across the fracture line to the next deployment site.
3. As illustrated in FIG. 7B:
  a. The long outer prong (310) and long inner prong (320) of the anchor (300) are partially driven into the bone to a depth such that the short outer prong (330) allows the suture (110) to pass beneath it.
  b. The surgeon sets tension in to suture (110) with the tensioning knob (620) in the instrument (660).

4. As illustrated in FIG. 7C:
  a. While holding the suture (110) under tension, a sleeve in the instrument (660) rotates the suture (110) around the short outer prong (330).
  b. The suture (110) is then completely secured by driving the all three prongs of the anchor (300) as deep as possible into the bone.
  c. Tension in the suture (110) is released via the tension release button (630).
5. As illustrated in FIG. 7D: The above steps are repeated until the desired "stitch" pattern across the fracture has been constructed. Most commonly, an I, V, N or W pattern is employed.

While several illustrative embodiments of the invention have been shown and described, numerous variations and alternate embodiments will occur to those skilled in the art, and can be made without departing from the spirit and scope of the invention as defined in the appended claims.

The invention claimed is:

1. A surgical anchoring system operable for securing a surgical cable, said surgical anchoring system comprising:
  a. A surgical cable and an "E" shaped staple, said staple having three prongs and a bridge,
  b. wherein each of said three prongs defines a longitudinal axis, wherein each of said three longitudinal axes are parallel to the other two, wherein said bridge is unitary with and perpendicular to each of said three longitudinal axes, said bridge defining a bridge axis that is perpendicular to each of said three longitudinal axes,
  c. wherein said "E" shaped staple is planar,
  d. said three prongs comprising a first outer prong, a middle prong, and a second outer prong, said first outer prong having a first length, said middle prong having a middle length, said first length being equal to said middle length, said second outer prong having second length, said second length being equal to both said first length and said middle length,
  e. a first space defined by a first void between the first outer prong and the middle prong, said first space having a first width defined by the perpendicular distance between the first outer prong and the middle prong, and a first arch defined by the first outer prong, the middle prong and the bridge, said first arch being an arc of a conical cross section, a second space defined by a second void between the second outer prong and the middle prong, said second space having a second width defined by the perpendicular distance between the second outer prong and the middle prong, and a second arch defined by the second outer prong, the middle prong and the bridge, said second arch being an arc of a conical cross section, wherein said first width is equal to said second width, and said first arch is identical to said second arch,
  f. wherein said surgical cable is comprised of a polymer core and a braided jacket, said surgical cable being operable for interleaving between said three prongs, said surgical cable having a diameter and a length, said diameter being perpendicular to said length, said diameter being smaller than said first and second widths, and wherein said diameter is mateable to both said first and second arches.

2. A surgical anchoring system operable for securing a surgical cable, said surgical anchoring system comprising:
  a. A surgical cable and a curved "E" shaped staple, said staple having three prongs and a bridge,
  b. wherein each of said three prongs defines a longitudinal axis, wherein each of said three longitudinal axes are parallel to the other two, wherein said bridge is unitary with and perpendicular to each of said three longitudinal axes, said bridge defining a bridge axis that is perpendicular to each of said three longitudinal axes,
  c. wherein said curve is defined by an arc of a conical cross section, wherein said arc has an axis of rotation and said axis of rotation is parallel to each of said three longitudinal axes,
  d. said three prongs comprising a first outer prong, a middle prong, and a second outer prong, said first outer prong having a first length, said middle prong having a middle length, said first length being equal to said middle length, said second outer prong having second length, said second length being equal to both said first length and said middle length,
  e. a first space defined by a first void between the first outer prong and the middle prong, said first space having a first width defined by the perpendicular distance between the first outer prong and the middle prong, and a first arch defined by the first outer prong, the middle prong and the bridge, said first arch being an arc of a conical cross section, a second space defined by a second void between the second outer prong and the middle prong, said second space having a second width defined by the perpendicular distance between the second outer prong and the middle prong, and a second arch defined by the second outer prong, the middle prong and the bridge, said second arch being an arc of a conical cross section, wherein said first width is equal to said second width, and said first arch is identical to said second arch,
  f. wherein said surgical cable is comprised of a polymer core and a braided jacket, said surgical cable being operable for interleaving between said three prongs, said surgical cable having a diameter and a length, said diameter being perpendicular to said length, said diameter being smaller than said first and second widths, and wherein said diameter is mateable to both said first and second arches.

3. A surgical anchoring system operable for securing a surgical cable, said surgical anchoring system comprising:
  a. A surgical cable and an "E" shaped staple, said staple having three prongs and a bridge,
  b. wherein each of said three prongs defines a longitudinal axis, wherein each of said three longitudinal axes are parallel to the other two, wherein said bridge is unitary with and perpendicular to each of said three longitudinal axes, said bridge defining a bridge axis that is perpendicular to each of said three longitudinal axes,
  c. wherein said "E" shaped staple is planar,
  d. said three prongs comprising a first outer prong, a middle prong, and a second outer prong, said first outer prong having a first length, said middle prong having a middle length, said first length being equal to said middle length, said second outer prong having second length, said second length being shorter than both said first length and said middle length by at least a distance equal to said second width,
  e. a first space defined by a first void between the first outer prong and the middle prong, said first space having a first width defined by the perpendicular distance between the first outer prong and the middle prong, and a first arch defined by the first outer prong, the middle prong and the bridge, said first arch being an arc of a conical cross section, a second space defined by a second void between the second outer prong and the middle prong, said second space having a second width defined by the perpendicular distance between the second outer prong and the middle prong, and a second arch defined by the second outer prong, the middle prong and the bridge, said second arch being an arc of a conical cross section, wherein said first width is equal to said second width, and said first arch is identical to said second arch, f. wherein said surgical cable is comprised of a polymer core and a braided jacket, said surgical cable being operable for interleaving between said three prongs, said surgical cable having a diameter and a length, said diameter being perpendicular to said length, said diameter being smaller than said first and second widths, and wherein said diameter is mateable to both said first and second arches.

4. A surgical anchoring system operable for securing a surgical cable, said surgical anchoring system comprising:

a. A surgical cable and a curved "E" shaped staple, said staple having three prongs and a bridge, b. wherein each of said three prongs defines a longitudinal axis, wherein each of said three longitudinal axes are parallel to the other two, wherein said bridge is unitary with and perpendicular to each of said three longitudinal axes, said bridge defining a bridge axis that is perpendicular to each of said three longitudinal axes, c. wherein said curve is defined by an arc of a conical cross section, wherein said arc has an axis of rotation and said axis of rotation is parallel to each of said three longitudinal axes, d. said three prongs comprising a first outer prong, a middle prong, and a second outer prong, said first outer prong having a first length, said middle prong having a middle length, said first length being equal to said middle length, said second outer prong having second length, said second length being shorter than both said first length and said middle length by at least a distance equal to said second width, e. a first space defined by a first void between the first outer prong and the middle prong, said first space having a first width defined by the perpendicular distance between the first outer prong and the middle prong, and a first arch defined by the first outer prong, the middle prong and the bridge, said first arch being an arc of a conical cross section, a second space defined by a second void between the second outer prong and the middle prong, said second space having a second width defined by the perpendicular distance between the second outer prong and the middle prong, and a second arch defined by the second outer prong, the middle prong and the bridge, said second arch being an arc of a conical cross section, wherein said first width is equal to said second width, and said first arch is identical to said second arch, f. wherein said surgical cable is comprised of a polymer core and a braided jacket, said surgical cable being operable for interleaving between said three prongs, said surgical cable having a diameter and a length, said diameter being perpendicular to said length, said diameter being smaller than said first and second widths, and wherein said diameter is mateable to both said first and second arches.

\* \* \* \* \*